(12) United States Patent
Nishihara et al.

(10) Patent No.: US 8,894,579 B2
(45) Date of Patent: Nov. 25, 2014

(54) ULTRASONIC DIAGNOSTIC APPARATUS AND CONTROLLING METHOD OF ULTRASONIC DIAGNOSTIC APPARATUS

(75) Inventors: Kuramitsu Nishihara, Otawara (JP); Shigemitsu Nakaya, Otawara (JP); Akihiro Kakee, Nasushiobara (JP); Kenichi Ichioka, Nasushiobara (JP); Chihiro Shibata, Nasushiobara (JP); Masao Takimoto, Otawara (JP); Atsushi Sumi, Otawara (JP); Muneki Kataguchi, Nasushiobara (JP); Takuya Sasaki, Nasu-gun (JP); Yoshihito Abe, Nasushiobara (JP); Yasushi Kamewada, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 757 days.

(21) Appl. No.: 12/697,681

(22) Filed: Feb. 1, 2010

(65) Prior Publication Data

US 2010/0198073 A1  Aug. 5, 2010

(30) Foreign Application Priority Data

Feb. 5, 2009  (JP) ................. 2009-025077

(51) Int. Cl.
*A61B 8/00* (2006.01)
*A61B 8/14* (2006.01)
*A61B 8/08* (2006.01)
*A61B 5/024* (2006.01)

(52) U.S. Cl.
CPC ............ *A61B 8/14* (2013.01); *A61B 8/0883* (2013.01); *A61B 8/0866* (2013.01); *A61B 5/02411* (2013.01); *A61B 8/483* (2013.01)
USPC ........................................... 600/443

(58) Field of Classification Search
USPC ................................... 600/437–461
See application file for complete search history.

(56) References Cited

U.S. PATENT DOCUMENTS

| 6,966,878 B2 | 11/2005 | Schoisswohl et al. |
| 6,980,844 B2 | 12/2005 | Schoisswohl |

(Continued)

FOREIGN PATENT DOCUMENTS

| JP | 2004-229958 | 8/2004 |
| JP | 2004-275223 | 10/2004 |

(Continued)

OTHER PUBLICATIONS

Office Action issued May 21, 2013 in Japanese Patent Application No. 2009-025077.

(Continued)

*Primary Examiner* — Elmer Chao
(74) *Attorney, Agent, or Firm* — Oblon, Spivak, McClelland, Maier & Neustadt, L.L.P.

(57) ABSTRACT

An ultrasonic diagnostic apparatus has a unit which sets a display region for displaying a 3D image, a unit which transmits and receives ultrasound waves, a unit which generates volume data, a unit, on the basis of the volume data, which sets an analysis region, a unit, on the basis of the data on the analysis region contained in the volume data, which analyzes a fluctuations in signal intensity over time, a unit, on the basis of the analysis result, which calculates a cardiac cycle, a unit, on the basis of the cardiac cycle and the volume data, which generates data set constructed by data with substantially equal cardiac cycle, and generates data sets corresponding to a plurality of cardiac cycles, and a unit which displays the 3D images based on the data sets as a moving image.

12 Claims, 10 Drawing Sheets

(56) References Cited

U.S. PATENT DOCUMENTS

| | | | |
|---|---|---|---|
| 2004/0042656 A1* | 3/2004 | Timor et al. | 382/171 |
| 2005/0267366 A1* | 12/2005 | Murashita et al. | 600/437 |
| 2006/0079783 A1* | 4/2006 | Clark | 600/450 |
| 2008/0044054 A1* | 2/2008 | Kim et al. | 382/100 |

FOREIGN PATENT DOCUMENTS

| | | |
|---|---|---|
| JP | 2005-74225 | 3/2005 |
| JP | 2006-61698 | 3/2006 |
| JP | 2006-231035 | 9/2006 |
| JP | 2008-12047 | 1/2008 |
| JP | 2008-142362 A | 6/2008 |

OTHER PUBLICATIONS

Office Action issued Aug. 13, 2013 in Japanese Patent Application No. 2009-025077.

* cited by examiner

DISTRIBUTION OF VARIANCES BASED ON
BRIGHTNESS VALUES IN HORIZONTAL DIRECTION

FIG. 5A

DISTRIBUTION OF VARIANCES BASED ON
BRIGHTNESS VALUES IN VERTICAL DIRECTION

FIG. 5B

DISTRIBUTION OF VARIANCES BASED ON
BRIGHTNESS VALUES IN DEPTH DIRECTION

ULTRASONIC DIAGNOSTIC APPARATUS AND CONTROLLING METHOD OF ULTRASONIC DIAGNOSTIC APPARATUS

BACKGROUND OF THE INVENTION

1. Field of the Invention

The present invention relates to an ultrasonic diagnostic apparatus and a controlling method of the ultrasonic diagnostic apparatus that generates a 3D image from a signal obtained by ultrasonic scanning using an ultrasonic probe.

2. Description of the Related Art

There has been provided a technology called a spatio temporal image correlation (STIC) that calculates a cycle of fluctuation in time of a subject from the 3D data collected in an ultrasonic diagnostic apparatus, and uses the calculated cycle of fluctuation to rearrange and display the data in cardiac cycles.

The STIC has been used mainly for obtaining a 3D image of a fetal heart and, distinctively, may display a movement of a fetal heart in real time without requiring heart-rate synchronization. The STIC uses a mechanically sweeping mechanical 4D probe to read periodical changes of the heart with 4D ultrasound, which is developed for the fetal heart, and thus detect heart rates of the fetus as cardiac cycles (which may be called heart rate value). The STIC is a system which an image is obtained by scanning to the entire heart in approximately 10 seconds, which volume data are synthesized in accordance with the cardiac cycles, and which a moving image constructed by images for one cardiac cycle is established. Since the STIC obtains images of 150 frames in one second, one scanning operation for 10 seconds save the data for 1,500 cross-sectional images. On the basis of the volume data containing approximately 40 cross-sectional images for each cardiac cycle, a 3D image set is reconfigured. The 3D image set is moved in series for 4D display.

An ultrasonic diagnostic apparatus applying the STIC is disclosed in Japanese Patent Application Publication No. 2005-74225.

However, the technology in the past extracts analysis sample data from the entire data contained in the volume data to estimate the cycles of fluctuation. Thus, when, for example, the heart of the fetus is scanned, real cardiac cycles may be different from the estimated cardiac cycles. The reasons for the difference may include that the data extracted as the analysis sample contains data on the other regions in addition to the data on the heart and components, such as a fetal movement and maternal cardiac cycles, excluding the beats of the fetal heart may mix therein as noise. This may lower the precision of the peak detection with autocorrelation or fast Fourier transform (FFT) analysis.

When correct cardiac cycles are not calculated, the technology in the past may require capturing the volume data by performing the 2D scanning (or live scanning) again, which increases the time required for examination.

SUMMARY OF THE INVENTION

The present invention was made in consideration of the aforementioned matters, and it is an object of the present invention to provide an ultrasonic diagnostic apparatus and a controlling method of the ultrasonic diagnostic apparatus that can improve the precision of estimation of cardiac cycles and generate and display 3D images of a fetal heart more simply.

The present invention was made in consideration of the aforementioned matters, and it is another object of the present invention to provide an ultrasonic diagnostic apparatus and a controlling method of the ultrasonic diagnostic apparatus that can improve the efficiency of generation of data of a moving image regarding a fetus.

To solve the above-described problems, the present invention provides the ultrasonic diagnostic apparatus comprising: a display region setting unit configured to set a display region for displaying a 3D image; a transmitting/receiving unit configured to transmit and receive ultrasound waves; a first generating unit configured to control the transmitting/receiving unit to perform a 3D scanning on the display region, and generate volume data; an analysis region setting unit configured to, on the basis of the volume data, set an analysis region to be used for calculation of a cycle of fluctuation over time; an analyzing unit configured to, on the basis of the data on the analysis region contained in the volume data, analyze a fluctuations in signal intensity over time; a calculating unit configured to, on the basis of the analysis result, detect a peak point of power, and calculate a cardiac cycle; a second generating unit configured to, on the basis of the cardiac cycle and the volume data, generate data set constructed by data with substantially equal cardiac cycle, and generate data sets corresponding to a plurality of cardiac cycles; and a display unit configured to perform a rendering processing on each data set of the data sets into a 3D image set, and display the 3D images as a moving image.

To solve the above-described problems, the present invention provides the controlling method of the ultrasonic diagnostic apparatus comprising steps of: display region setting which sets a display region for displaying a 3D image; first generating, on the basis of a transmitting and reception of ultrasound waves, which controls the step of transmitting/receiving to perform a 3D scanning on the display region, and generates volume data; analysis region setting, on the basis of the volume data, which sets an analysis region to be used for calculation of a cycle of fluctuation over time; analyzing, on the basis of the data on the analysis region contained in the volume data, which analyzes a fluctuations in signal intensity over time; calculating, on the basis of the analysis result, which detects a peak point of power, and calculates a cardiac cycle; second generating, on the basis of the cardiac cycle and the volume data, which generates data set constructed by data with substantially equal cardiac cycle, and generates data sets corresponding to a plurality of cardiac cycles; and displaying which performs a rendering processing on each data set of the data sets into a 3D image set, and displays the 3D images as a moving image.

DESCRIPTION OF THE PREFERRED EMBODIMENTS

An embodiment of an ultrasonic diagnostic apparatus and a controlling method of the ultrasonic diagnostic apparatus according to the present invention will be described with reference to accompanying drawings.

Figure 1:
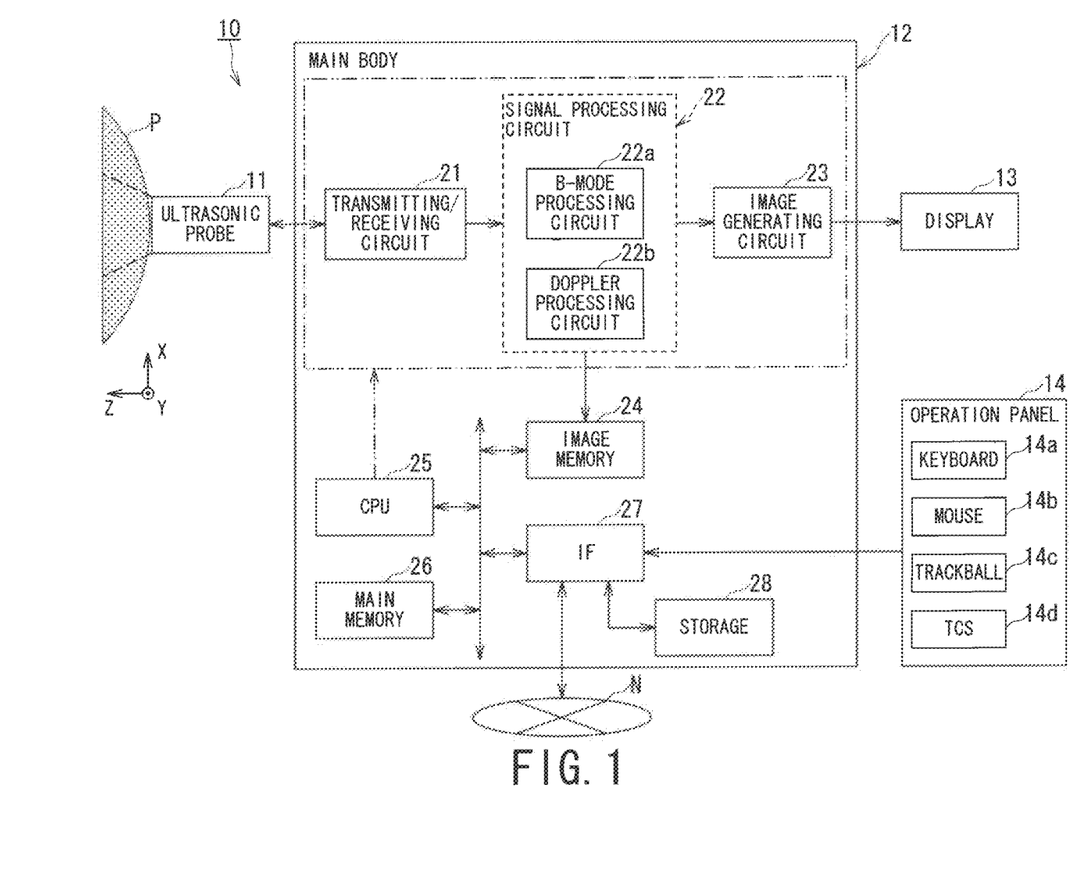
FIG. 1 is a schematic diagram illustrating a configuration of ultrasonic diagnostic apparatus of a present embodiment.

FIG. 1 is a schematic diagram illustrating a configuration of ultrasonic diagnostic apparatus of the present embodiment.

FIG. 1 illustrates an ultrasonic diagnostic apparatus 10 of the present embodiment applying an STIC. The ultrasonic diagnostic apparatus 10 roughly includes an ultrasonic probe 11, a main body 12, a display 13 and an operation panel 14.

The ultrasonic probe 11 has a plurality of piezoelectric transducers which transmit ultrasonic pulses to a three-dimensional (3D) scan region including a subject within a patient P on the basis of drive pulses from the main body 12, receive the echoes corresponding to the transmitted ultrasonic pulses and convert it to electric signals. When ultrasonic pulses are transmitted from the piezoelectric transducers in the ultrasonic probe 11 to the scan region, the ultrasonic beams formed by the ultrasonic pulses are successively reflected by a discontinuous plane of acoustic impedance of a body tissue. The reflected echo is received by the piezoelectric transducer set. The received echoes are converted by the piezoelectric transducers in echo signals. The echo signals have amplitudes that depend on the differences in acoustic impedance on the reflecting discontinuous plane. When reflected by a moving surface of a blood flow or a heart wall, the echo corresponding to the transmitted ultrasonic pulses depends on a velocity component in the direction of ultrasonic transmission by a moving object because of a Doppler effect and is shifted in frequency.

The ultrasonic probe 11 may be, for example, a mechanical 3D probe or a two-dimensional (2D) probe (or matrix array probe). The mechanical 3D probe may be a probe that can mechanically sweep many (such as 100 to 200) piezoelectric transducers only arranged in the X-axis direction (or azimuth direction) or a probe that can mechanically sweep many piezoelectric transducers arranged in the X-axis direction and a few (such as three) piezoelectric transducers arranged in the Y-axis direction (or elevation direction). The 2D probe is a probe having many piezoelectric transducers arranged in both of the X-axis direction and Y-axis direction.

The ultrasonic probe 11 being the mechanical 3D probe electronically focuses with many piezoelectric transducers arranged in the X-axis direction in order to converge ultrasonic pulses into the X-axis direction and form a correct ultrasonic beam extending in the Z-axis direction (or depth direction). On the other hand, the ultrasonic probe 11 being the mechanical 3D probe preferably includes acoustic lenses on the ultrasound irradiation sides of one piezoelectric transducer in the Y-axis direction or a concave transducer instead of the piezoelectric transducer in order to converge ultrasonic pulses into the Y-axis direction and forms a correct ultrasonic beam extending in the Z-axis direction. Alternatively, the ultrasonic probe 11 being the mechanical 3D probe may include an acoustic lens on the ultrasound irradiation side of a few piezoelectric transducers in the Y-axis direction or may change the number of times of driving a few piezoelectric transducers in the Y-axis direction in accordance with the positions in the Z-axis direction of the focal point in order to converge ultrasonic pulses into the Y-axis direction and form a correct ultrasonic beam extending in the Z-axis direction. In order to use the mechanical 3D probe to scan plural scan cross-sections, plural 2D cross-sections (which are X-Z cross-sections) are scanned with the ultrasonic beam formed by the ultrasonic pulses by sweeping the piezoelectric transducers.

The ultrasonic probe 11 being the 2D probe electronically focuses with many piezoelectric transducers arranged in the X-axis direction and Y-axis direction in order to converge ultrasonic pulses into the X-axis direction and Y-axis direction and form a correct ultrasonic beam extending in the Z-axis direction. In order to use the 2D probe to scan plural scan cross-sections, plural X-Z cross-sections are scanned with the ultrasonic beam formed by the ultrasonic pulses by electronically shifting the transmission plane of ultrasonic pulses in the Y-axis direction.

The main body 12 includes a transmitting/receiving circuit 21, a signal processing circuit 22, an image generating circuit 23, an image memory 24, a central processing unit (CPU) 25, a main memory 26, an interface (IF) 27 and a storage 28. According to the present embodiment, the transmitting/receiving circuit 21, signal processing circuit 22 and image generating circuit 23 are included in an integrated circuit. However, all or a part of them may function by the execution of software programs modularized in software.

The transmitting/receiving circuit 21 includes a transmitting circuit and a receiving circuit, not shown. The transmitting circuit has a pulser circuit, a transmission delay circuit and a trigger generating circuit, not shown. The pulser circuit repetitively generates a rate pulse for forming transmit ultrasound at a predetermined rate frequency fr [Hz] (cycle: 1/fr [second]). The transmission delay circuit converges ultrasound into a beam for each channel and gives a delay time required for determining the transmission directivity to each rate pulse. The trigger generating circuit applies a drive pulse to piezoelectric transducers in the ultrasonic probe 11 at the time based on the rate pulse.

Note that the transmitting circuit of the transmitting/receiving circuit 21 has a function that can instantly change the transmission frequency, transmission drive voltage (acoustic pressure), transmission pulse rate, scan region and the number of times of flashing in accordance with an instruction by the CPU 25. Particularly, the acoustic pressure may be changed by a linear-amplifier type transmitting unit that can instantly change the value or a mechanism that electrically switches among plural power supply units.

The receiving circuit of the transmitting/receiving circuit 21 has an amplifier, a reception delay circuit, an analog to digital (A/D) converting circuit and an adding circuit, not shown. The amplifier amplifies an echo signal captured through the ultrasonic probe 11 for each channel. The reception delay circuit gives a delay time required for determining the reception directivity to the echo signal amplified by the amplifier. The A/D converting circuit converts the echo signal output from the reception delay circuit to a digital signal. The adding circuit performs adding processing on the digital echo signal. The addition by the adding circuit can emphasize the reflected component from the direction according to the reception directivity of the echo signal. Thus, the reception directivity and the transmission directivity form a synthetic beam to be ultrasonically transmitted and/or received, and a radio frequency (RF) signal can be generated.

The signal processing circuit 22 includes a B-mode processing circuit 22a and a Doppler processing circuit 22b. The B-mode processing circuit 22a performs logarithmic amplification and envelop detection processing on the RF signal obtained by the transmitting/receiving circuit 21 to generate a B-mode image in which the signal intensity is expressed by brightness. In this case, the detection frequency may be changed to change the frequency band for visualization. The detection processing with two detection frequencies may be performed in parallel on one received data piece.

The Doppler processing circuit 22b performs frequency analysis on the velocity information from the RF signal obtained by the transmitting/receiving circuit 21, extracts the echo component of a blood flow, a tissue or a contract material attributed to a Doppler effect, and obtains blood flow information such as an average velocity, a variance and a power, with regard to multiple points. The Doppler processing circuit 22b generates the blood flow information such as an average velocity image, a variance image, a power image and a Doppler image combining them.

The image generating circuit 23 converts a cross-sectional image of a scan line signal sequence of ultrasonic scanning, which is output from the signal processing circuit 22, into a cross-sectional image of a scan line signal sequence in a general video format typified in, for example, televisions. The image generating circuit 23 includes a memory (not shown) that stores an image. For example, after a diagnosis, an operator (or a user) can call up an image recorded during an examination. Further, the image generating circuit 23 forms volume data on the basis of the cross-sectional images.

The image memory 24 is a storage device that stores an image output from the signal processing circuit 22 and image generating circuit 23. The image memory 24 stores in parallel images obtained under different transmission and reception conditions. The image memory 24 stores what is called raw data, which are a cross-sectional image in the data format before the conversion, and output from the signal processing circuit 22 and/or the volume data based on the cross-sectional image. The image memory 24 may store the volume data based on a cross-sectional image in the data format after the video-format conversion, which is output from the image generating circuit 23 and/or a cross-sectional image in the data format after the video-format conversion, which is output from the image generating circuit 23.

The CPU 25 is a control unit having an integrated circuit (LSI: large scale integration) contained in a package in which an electronic circuit configured by a semiconductor has plural terminals. The CPU 25 has a function of executing a program stored in the main memory 26. The CPU 25 has a function of loading into the main memory 26 and executing a program stored in the storage 28 or a program transferred from a network N, and received by the IF 27 and installed in the storage 28.

The main memory 26 is a storage device having both functions of a read only memory (ROM) and a random access memory (RAM), for example. The main memory 26 has a function of storing an initial program loading (IPL), a basic input/output system (BIOS) and data and possibly being used as a work memory of the CPU 25 or for temporary storage of data.

The IF 27 includes a connector according to parallel connection specifications and/or serial connection specifications. The IF 27 is an interface relating to the operation panel 14, a basic network N of a hospital, such as a local area network (LAN), and the storage 28, for example. The image generated by the main body 12 can be transferred through the IF 27 to the network N to other apparatus.

The storage 28 is a storage device having a metallic disk formed by coating or evaporating a magnetic substance and being irremovably and internally installed in a reader (not shown). The storage 28 has a function of storing programs (including an application program and an operating system (OS)) installed in the main body 12. The OS may provide a graphical user interface (GUI) allowing an operator to perform a basic operation through the operation panel 14 with reference to many graphically displayed pieces of information.

The main memory 26 or storage 28 stores a control program, diagnostic information (such as a patient identification (ID) and a doctor's opinion), a diagnostic protocol, a transmission/reception condition and other data sets. The data stored in the main memory 26 or storage 28 may be transferred through the IF 27 and over the network N.

The display 13 may be a liquid crystal display or a cathode ray tube (CRT), for example. The display 13 has a function of displaying 3D data along with text information on various parameters and the corresponding scale, for example, on the basis of a video signal from the image generating circuit 23.

The operation panel 14 may include a keyboard 14a, a mouse 14b, a trackball 14c and a touch command screen (TCS) 14d. The operation panel 14 has a function of inputting an instruction from an operator, such as an instruction to set a region of interest (ROI) through the IF 27 to the CPU 25.

Figure 2:
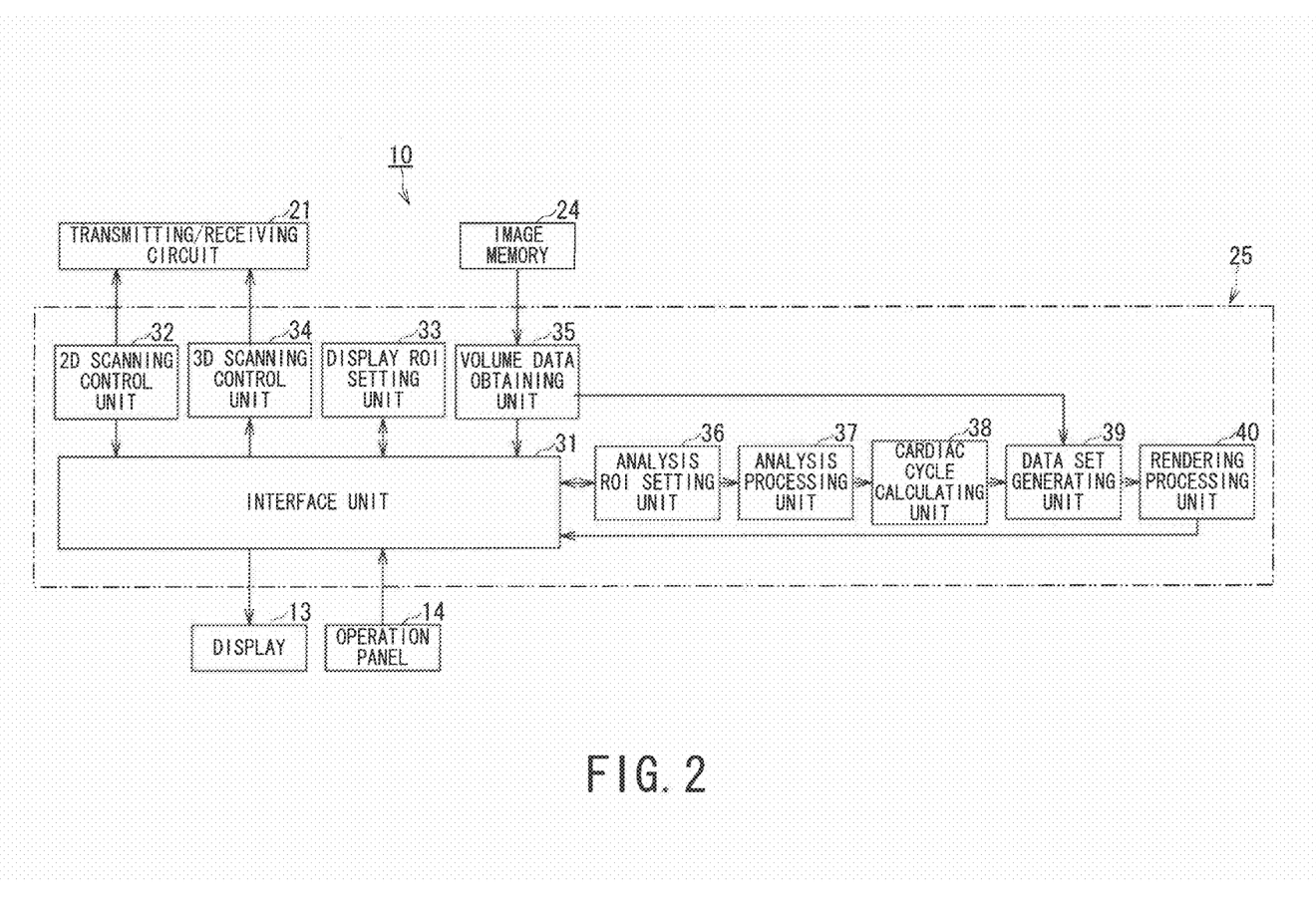
FIG. 2 is a block diagram illustrating functions of the ultrasonic diagnostic apparatus of the present embodiment.

FIG. 2 is a block diagram illustrating functions of the ultrasonic diagnostic apparatus 10 of the present embodiment.

The execution of programs by the CPU 25 illustrated in FIG. 1 causes the ultrasonic diagnostic apparatus 10 to have an interface unit 31, a 2D scanning control unit 32, a display ROI setting unit 33, a 3D scanning control unit 34, a volume data obtaining unit 35, an analysis ROI setting unit 36, an analysis processing unit 37, a cardiac cycle calculating unit 38, a data set generating unit 39 and a rendering processing unit 40. According to the present embodiment, the units 31 to 40 are caused to function by the execution of software programs modularized in software. However, all or a part of them may be configured by hardware such as an integrated circuit.

The interface unit 31 is an interface such as the GUI. The GUI may mostly graphically display on the display 13 to an operator, whereby a basic operation can be performed through the operation panel 14.

The 2D scanning control unit 32 has a function of, if 2D scanning is instructed from the operation panel 14 through the interface unit 31, controlling the transmitting/receiving circuit 21 so as to irradiate ultrasound to a 2D region including the vicinity of the fetal heart to perform 2D scanning (live scanning).

The display ROI setting unit 33 has a function of, during 2D scanning by the 2D scanning control unit 32, defining a region including the fetal heart on the 2D image displayed through the image generating circuit 23 (illustrated in FIG. 1) as a display ROI of a 3D image (4D display). The display ROI setting unit 33 sets a display ROI in accordance with the signal input through the interface unit 31 by an operator using the operation panel 14 on the display screen of a 2D image.

The 3D scanning control unit 34 has a function of, when 3D scanning is instructed from the operation panel 14 through the interface unit 31, controlling the transmitting/receiving circuit 21 so as to irradiate ultrasound to a 3D region with the display ROI set by the display ROI setting unit 33 in the sweep direction to execute the 3D scanning. The 3D scanning control unit 34 causes to scan the entire fetal heart for a predetermined period of time such as 10 to 15 seconds.

The volume data obtaining unit 35 has a function of obtaining (or reading) the volume data formed by the display ROI stored in the image memory 24 by the 3D scanning control unit 34.

The analysis ROI setting unit 36 has a function of defining a 3D analysis ROI to be used for cardiac-cycle analysis on the basis of brightness information in the volume data obtained by the volume data obtaining unit 35. The analysis ROI setting unit 36 according to a first example manually sets the 3D analysis ROI on the basis of the volume data. In this case, the analysis ROI setting unit 36 causes to display a scan cross-sectional image (side-A image) and sets a side-A analysis ROI in accordance with the signal input through the interface unit 31 by an operator using the operation panel 14 on the side-A image. The analysis ROI setting unit 36 causes to display a cross-sectional image (side-B image) of the cross-sectional orthogonal to the scan plane and sets a side-B analysis ROI in accordance with the signal input through the interface unit 31 by an operator using the operation panel 14 on the side-B image.

Figure 3:
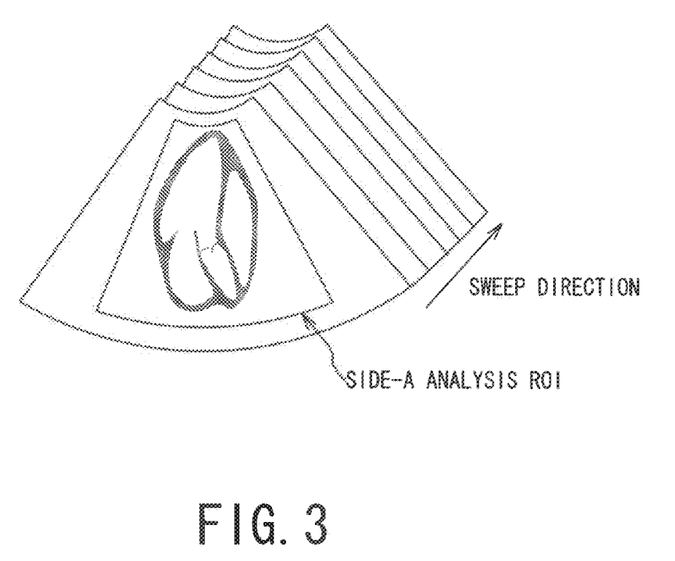
FIG. 3 is a diagram illustrating a display example of a side-A analysis ROI set on a side-A image.
Figure 4:
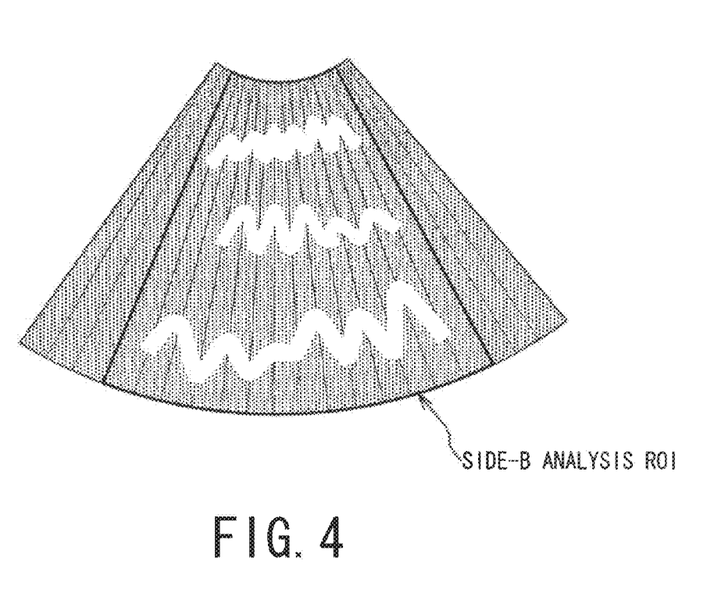
FIG. 4 is a diagram illustrating a display example of a side-B analysis ROI set on a side-B image.

FIG. 3 is a diagram illustrating a display example of the side-A analysis ROI set on a side-A image. FIG. 4 is a diagram illustrating a display example of the side-B analysis ROI set on a side-B image.

On the side-A image illustrated in FIG. 3, an operator may operate the operation panel 14 to change and/or move the frame indicating a side-A analysis ROI to be displayed so that the analysis ROI setting unit 36 can set a side-A analysis ROI. On the side-B image illustrated in FIG. 4, an operator may operate the operation panel 14 to change and/or move the frame indicating a side-B analysis ROI to be displayed so that the analysis ROI setting unit 36 can set a side-B analysis ROI.

The analysis ROI setting unit 36 according to a second example automatically sets a 3D analysis ROI on the basis of the volume data. The fetal heart moves actively, and a heart wall changes brightness values with a heart chamber between a high brightness and a low brightness over time. Thus, the brightness of the region having the fetal heart changes largely over time. This increases the variance of the brightness of the region having the fetal heart, compared with the other regions. Therefore, by obtaining the brightness variance, the region having the fetal heart can be extracted.

Figure 5A:
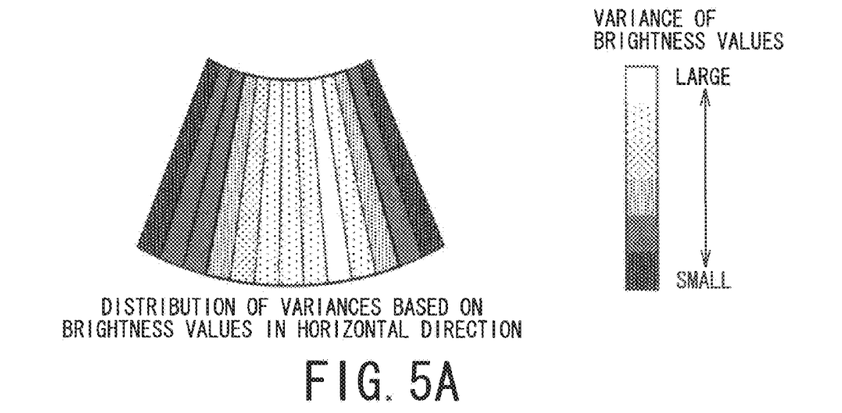
FIGS. 5A, 5B and 5C are conceptual diagrams illustrating an example of an automatic defining method for an analysis ROI.
Figure 5B:
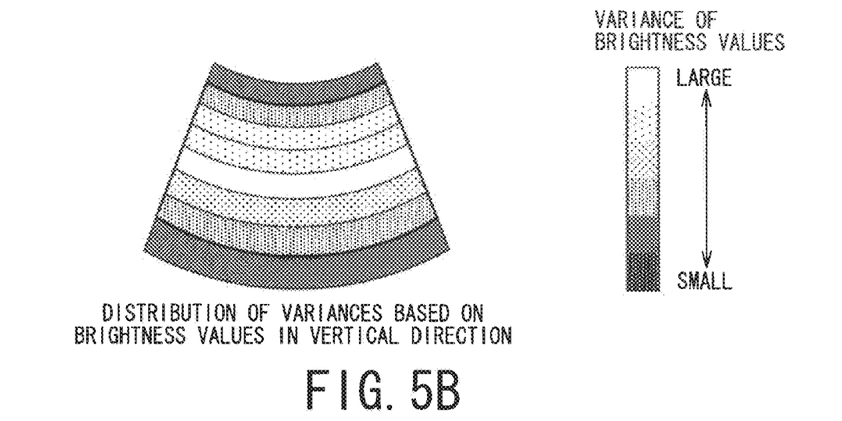
Figure 5C:
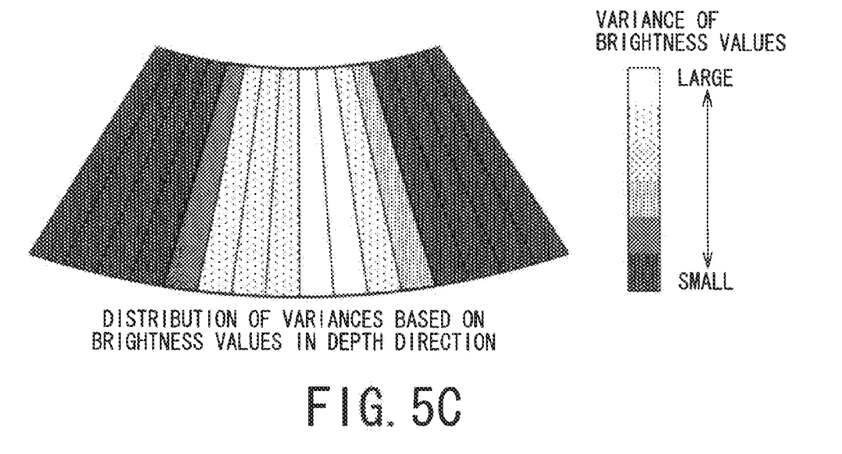

FIG. 5A, FIG. 5B and FIG. 5C are conceptual diagrams illustrating an example of an automatic defining method for an analysis ROI.

FIG. 5A is a diagram illustrating a distribution of variances based on brightness values in a horizontal direction. The distribution diagram is divided by shades of the magnitudes of the variance values, which are obtained for brightness value sets corresponding to the shown vertical lines on the basis of the side-A image. Obtaining the variances of the brightness values at the vertical lines on the side-A image from the left end to the right end of the side-A image, the region having the fetal heart has a higher variance value than the other region, as illustrated in FIG. 5A. Thus, referring to FIG. 5A, the fetal heart may be estimated to exist on the vertical lines corresponding to the variance values equal to or higher than threshold value obtained from an average value, for example, of the variance values at all vertical lines. Therefore, the vertical lines corresponding to the variance values beyond the threshold value can be automatically set as a side-A analysis ROI.

FIG. 5B is a diagram illustrating a distribution of variances based on brightness values in a vertical direction. The distribution diagram is divided by shades of the magnitudes of the variance values, which are obtained for brightness value sets corresponding to the shown horizontal lines on the basis of the side-A image. Referring to FIG. 5B, like the description referring to FIG. 5A, the fetal heart may be estimated to exist on the horizontal lines corresponding to the variance values equal to or higher than the threshold value obtained from an average value, for example, of the variance values at all horizontal lines. Therefore, the horizontal lines corresponding to the variance values beyond the threshold value can be automatically set as a side-A analysis ROI.

FIG. 5C is a diagram illustrating a distribution of variances based on brightness values in a depth direction. The distribution diagram is divided by shades of the magnitudes of the variance values, which are obtained for brightness value sets corresponding to the shown vertical lines on the basis of the side-B image. Referring to FIG. 5C, like the description referring to FIG. 5A, the fetal heart may be estimated to exist on the vertical lines corresponding to the variance values equal to or higher than the threshold value obtained from an average value, for example, of the variance values at all vertical lines. Therefore, the vertical lines corresponding to the variance values beyond the threshold value can be automatically set as a side-B analysis ROI.

Defining a side-A analysis ROI and a side-B analysis ROI on the biplane display of FIG. 5A and FIG. 5C or FIG. 5B and FIG. 5C allows the automatic definition of the 3D analysis ROI. The automatic defining method for a 3D analysis ROI is given for the illustration purpose only, and the other methods may be used to obtain the region having the fetal heart and automatically set a 3D analysis ROI.

The analysis processing unit 37 illustrated in FIG. 2 has a function of performing analysis processing such as autocorrelation and fast Fourier transform (FFT) analysis on the fluctuations in signal intensity over time on the basis of the data on the part within a 3D analysis ROI set by the analysis ROI setting unit 36.

The cardiac cycle calculating unit 38 has a function of detecting a peak point of power and calculating the cardiac cycle (140 to 200 [bpm]) of a fetus on the basis of the frequency spectrum as an analysis result generated by the analysis processing unit 37.

Figure 6:
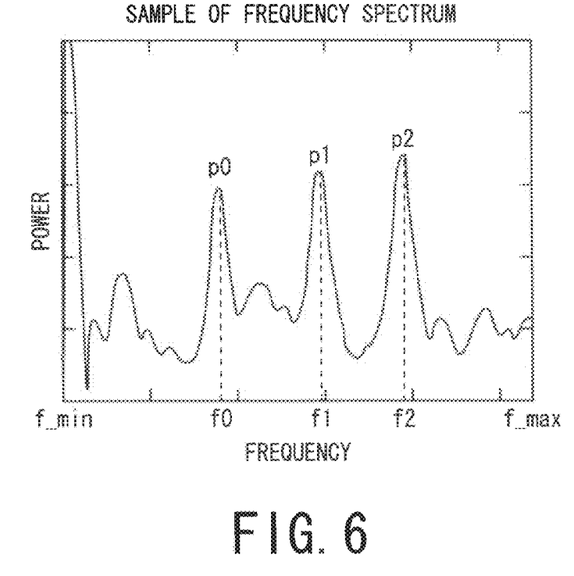
FIG. 6 is a diagram illustrating an example of a frequency spectrum corresponding to the related art.

FIG. 6 is a diagram illustrating an example of a frequency spectrum corresponding to the related art.

In the related art, a maximum peak p0 has been detected from power values at frequencies in a predetermined frequency range f_min to f_max, and a heart rate of a fetus has been calculated by handling the frequency f0 at the peak p0 as a cardiac cycle.

Figure 9:
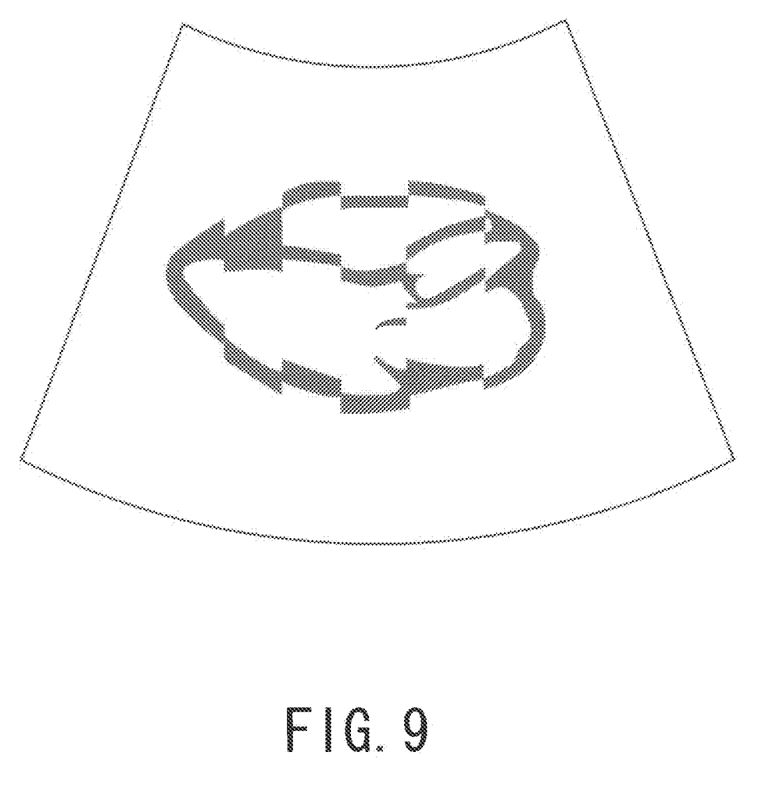
FIG. 9 is a conceptual diagram of a 3D image of the fetal heart, which is generated when the heart rate is miscalculated.

However, other frequency components such as a fetal movement may mix thereinto, and large power values may also occur at other frequencies such as peaks p1 and p2 excluding the peak p0. Thus, when the components at the peaks p1 and p2 are higher than that at the peak p0, the frequencies f1 and f2, which are frequencies excluding the cardiac cycle, might be miscalculated as a real fetal heart rate, instead of the frequency f0. As a result, the correct heart rate is not used to reconstruct the volume data, and it is difficult to obtain a correct moving image. FIG. 9 illustrates a conceptual diagram of a 3D image of the fetal heart, which is generated when the heart rate is miscalculated (where the frequency f0 at the peak p0 is not equal to the fetal heart rate).

Figure 7:
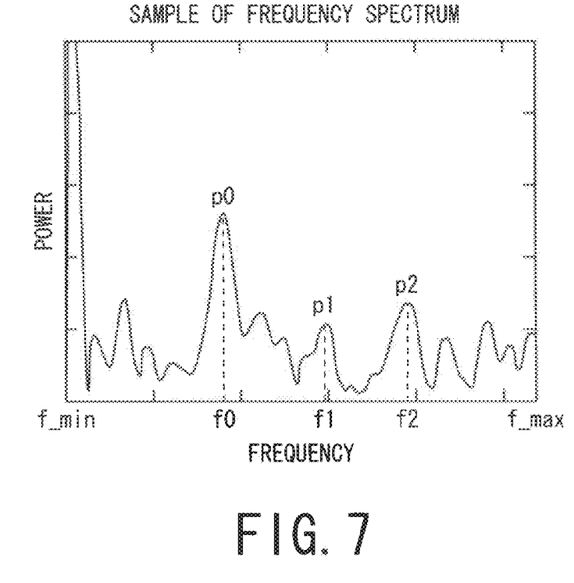
FIG. 7 is a diagram illustrating an example of a frequency spectrum corresponding to the present embodiment.

FIG. 7 is a diagram illustrating an example of a frequency spectrum corresponding to the present embodiment.

Figure 8:
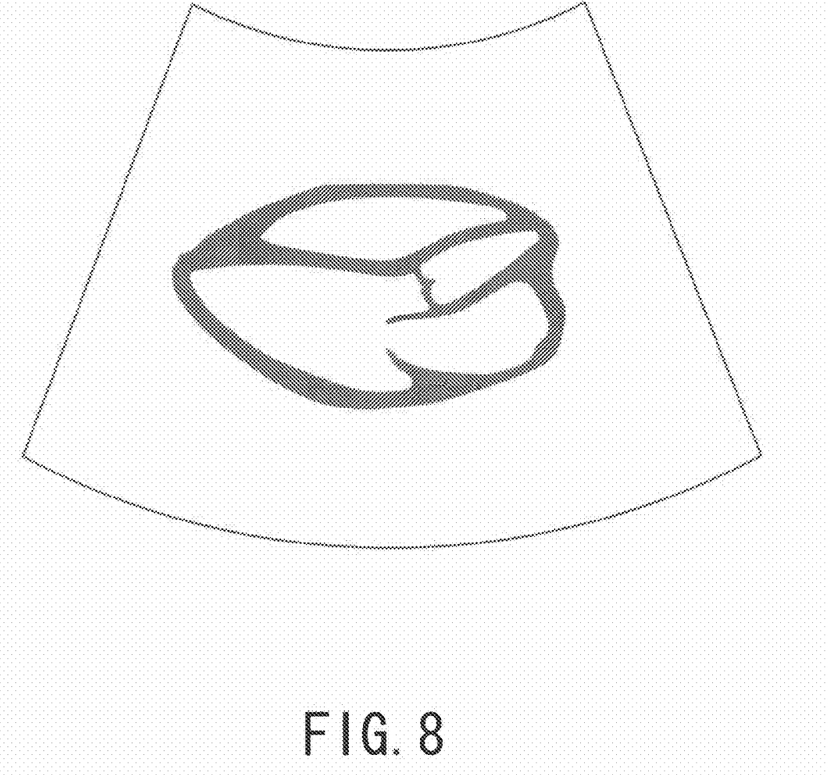
FIG. 8 is a conceptual diagram of a 3D image of a fetal heart, which is generated when a heart rate is correctly calculated.

The frequency spectrum illustrated in FIG. 7, which is the analysis result by the analysis processing unit 37, has lower components at the peaks p1 and p2, compared with the frequency spectrum in the past illustrated in FIG. 6. Thus, the heart rate can be correctly calculated. FIG. 8 illustrates a conceptual diagram of the 3D image of the fetal heart, which is generated when the heart rate is correctly calculated (where the frequency f0 at the peak p0 is equal to the fetal heart rate).

The data set generating unit 39 illustrated in FIG. 2 has a function of generating data set group for each substantially equal cardiac cycle from the volume data obtained by the volume data obtaining unit 35 on the basis of the cardiac cycles calculated by the cardiac cycle calculating unit 38.

Figure 10:
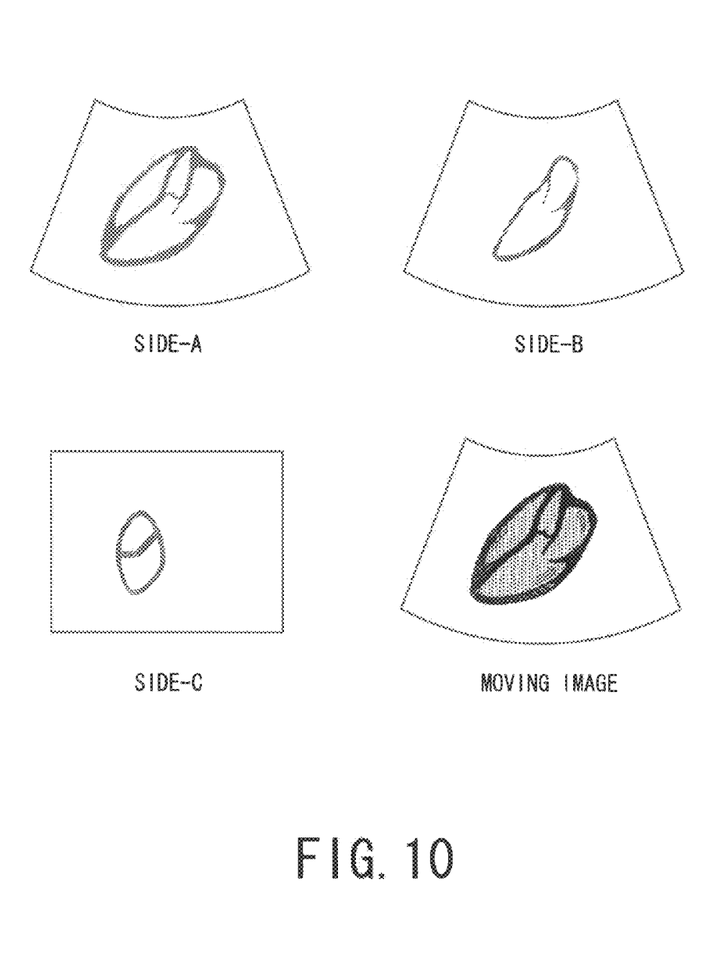
FIG. 10 is a diagram illustrating an example of multiplane display of a snapshot of a moving image to be displayed.

The rendering processing unit 40 has a function of performing rendering processing on data set groups for cardiac cycles into a 3D image set and displaying the 3D image set as a moving image on the display 13. FIG. 10 is a diagram illustrating an example of multiplane display of a snapshot (or one still image) of the moving image to be displayed.

Figure 11:
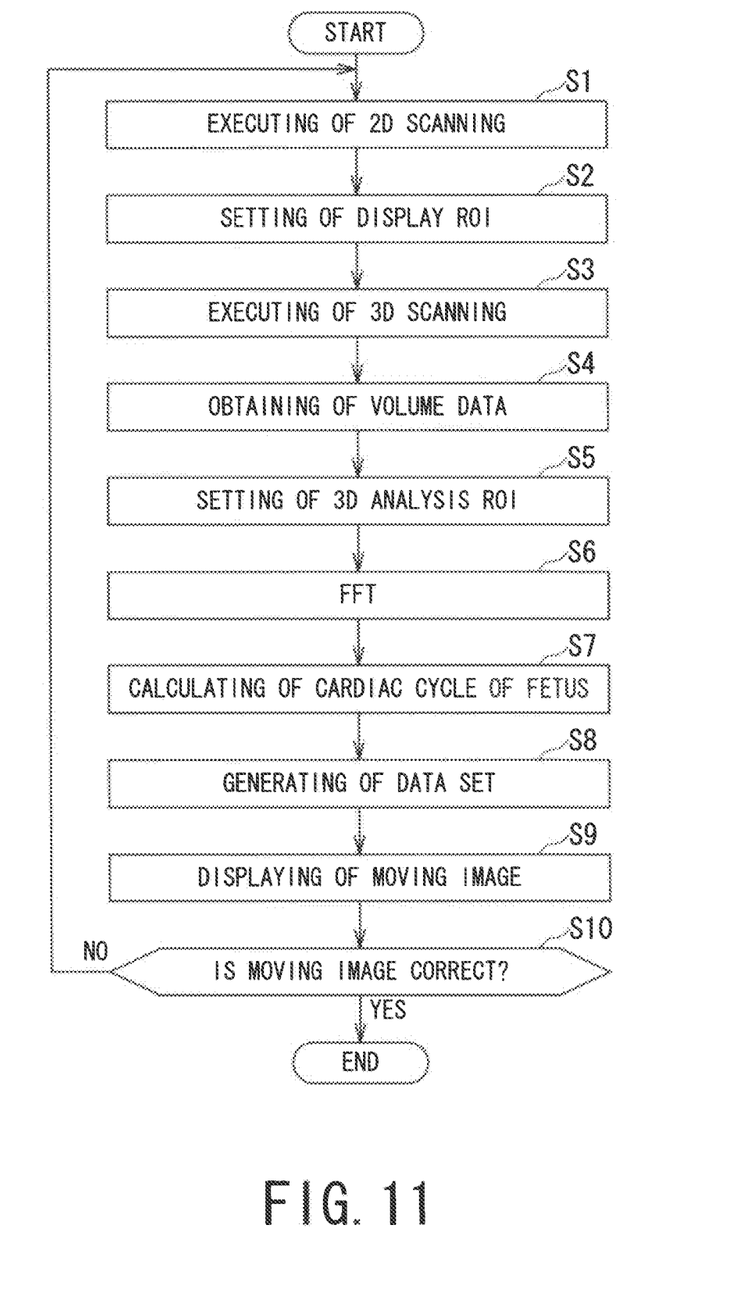
FIG. 11 is a flowchart illustrated a first operation by the ultrasonic diagnostic apparatus of the present embodiment.

Next, a first operation (or step) by the ultrasonic diagnostic apparatus of the present embodiment will be described with reference to the flowchart illustrated in FIG. 11.

If an operator uses the operation panel 14 to instruct 2D scanning, the ultrasonic diagnostic apparatus 10 controls the transmitting/receiving circuit 21 so as to irradiate ultrasound to a 2D region including the vicinity of the fetal heart and cause to execute 2D scanning (live scanning) (step S1).

During the 2D scanning in step S1, the ultrasonic diagnostic apparatus 10 sets a region including the fetal heart on the 2D image to be displayed through the image generating circuit 23 as a display ROI being a 3D image (step S2). The display ROI set by step S2 is based on the signal input by an operator using the operation panel 14 on the display screen of a 2D image.

Next, if an operator uses the operation panel 14 to instruct 3D scanning, the ultrasonic diagnostic apparatus 10 controls the transmitting/receiving circuit 21 so as to irradiate ultrasound to the 3D region with the display ROI set in step S2 in the sweep direction and cause to execute the 3D scanning (step S3). In step S3, the entire fetal heart is scanned in approximately 10 seconds.

Next, the ultrasonic diagnostic apparatus 10 obtains a volume data stored in the image memory 24 by the 3D scanning in step S3 (step S4).

Next, the ultrasonic diagnostic apparatus 10 sets the 3D analysis ROI to be used for cardiac-cycle analysis on the basis of the volume data obtained by step S4 (step S5). In step S5, the analysis ROI may be set manually on the basis of the volume data, as described above, or may be set automatically.

Alternatively, in step S5, as illustrated in FIG. 9, the ultrasonic diagnostic apparatus 10 may determine whether a 3D analysis ROI is to be set automatically or not (step S5a). If YES in step S5a, the ultrasonic diagnostic apparatus 10 may automatically set a 3D analysis ROI (step S5b). If NO, the ultrasonic diagnostic apparatus 10 may manually set a 3D analysis ROI (step S5c).

Next, on the basis of the data on the part within the 3D analysis ROI set by step S5, the ultrasonic diagnostic apparatus 10 performs autocorrelation or Fast Fourier transform (FFT) analysis on the fluctuations in signal intensity over time (step S6). On the basis of the frequency spectrum, which is the analysis result generated by step S6, the ultrasonic diagnostic apparatus 10 detects a peak point of power and calculates the cardiac cycle (140 to 200 [bpm]) of the fetus (step S7).

Next, on the basis of the cardiac cycle calculated by step S7, the ultrasonic diagnostic apparatus 10 generates data set groups for substantially equal cardiac cycles from the volume data (step S8). The ultrasonic diagnostic apparatus 10 performs rendering processing on the data set groups for cardiac cycles into 3D image sets and causes the display 13 to display the 3D image set as a moving image (step S9).

The ultrasonic diagnostic apparatus 10 determines whether the moving image displayed in step S9 is correct or not on the basis of the signal input by an operator using the operation panel 14 (step S10). If the determination in step S10 results in YES, that is, if it is determined that the moving image displayed in step S9 is correct, as illustrated in FIG. 8, the ultrasonic diagnostic apparatus 10 ends the operation.

If, on the other hand, the determination in step S10 results in NO, that is, if it is determined that the moving image displayed in step S9 is not correct, as illustrated in FIG. 9, the ultrasonic diagnostic apparatus 10 performs the 2D scanning again in order to change the moving image to be displayed (step S1).

Figure 12:
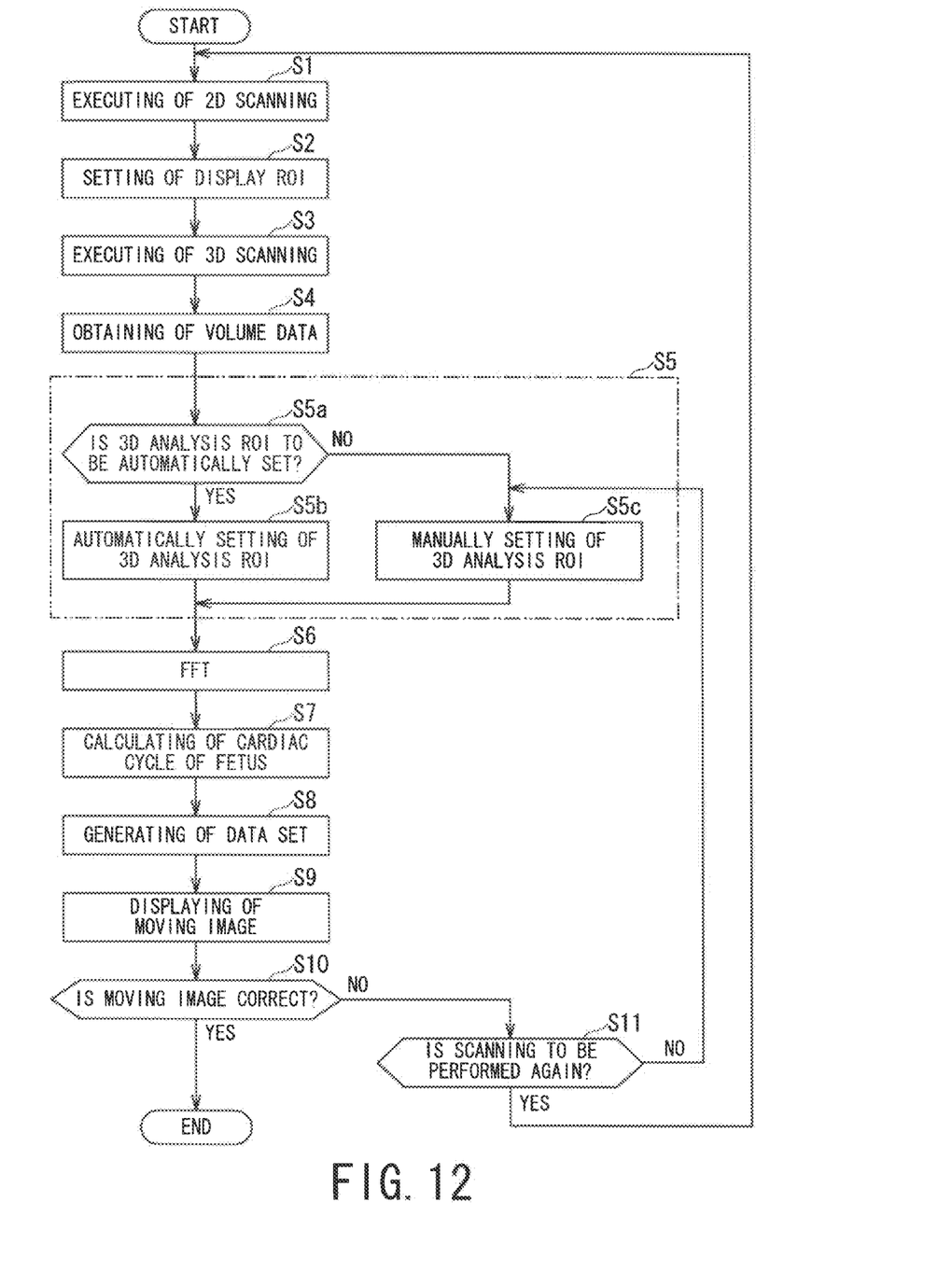
FIG. 12 is a flowchart illustrated a second operation by the ultrasonic diagnostic apparatus of the present embodiment.

Next, a second operation by the ultrasonic diagnostic apparatus of the present embodiment will be described with reference to the flowchart illustrated in FIG. 12. In the description and illustration of the second operation by the ultrasonic diagnostic apparatus of the present embodiment illustrated in FIG. 12, like numerals reference like operations to those in the operation illustrated in FIG. 11, and the description will be omitted.

On the basis of the signal input by an operator using the operation panel 14, the ultrasonic diagnostic apparatus 10 determines whether a 3D analysis ROI is to be automatically set or not (step S5a). If the determination in step S5a results in YES, that is, if it is determined that a 3D analysis ROI is to be automatically set, the ultrasonic diagnostic apparatus 10 automatically sets a 3D analysis ROI on the basis of the volume data obtained in step S4 (step S5b).

If, on the other hand, the determination in step S5a results in NO, that is, if it is determined that a 3D analysis ROI is not to be automatically set, the ultrasonic diagnostic apparatus 10 manually sets a 3D analysis ROI on the basis of the signal input by an operator using the operation panel 14 (step S5c).

On the basis of the signal input by an operator using the operation panel 14, the ultrasonic diagnostic apparatus 10 determines whether the moving image displayed in step S9 is correct or not (step S10). If the determination in step S10 results in YES, that is, if it is determined that the moving image displayed in step S9 is correct, as illustrated in FIG. 8, the ultrasonic diagnostic apparatus 10 ends the operation.

If, on the other hand, the determination in step S10 results in NO, that is, if it is determined that the moving image displayed in step S9 is not correct, as illustrated in FIG. 9, the ultrasonic diagnostic apparatus 10 determines whether the scanning is to be performed again or not on the basis of the signal input by an operator using the operation panel 14 (step S11). If the determination in step S11 results in YES, that is, if it is determined that the scanning is to be performed again, the ultrasonic diagnostic apparatus 10 performs the 2D scanning again (step S1).

If, on the other hand, the determination in step S11 results in NO, that is, if the scanning is not to be performed again, the ultrasonic diagnostic apparatus 10 manually sets a 3D analysis ROI on the basis of the signal input by an operator using the operation panel 14 (step S5c).

In the ultrasonic diagnostic apparatus 10 of the present embodiment, the region to be used for cardiac-cycle analysis is limited by the analysis ROI setting unit 36. This can minimize the reduction in precision of detection due to the other components, such as a fetal movement, than the beats of the fetal heart, and allows analysis with higher precision. As a result, the ultrasonic diagnostic apparatus 10 can display correct 3D images (4D display). In other words, the ultrasonic diagnostic apparatus 10 can improve the precision of estimation of cardiac cycles and allows more simple generation and display of 3D images of the fetal heart.

In the second operation using the ultrasonic diagnostic apparatus 10 of the present embodiment (described with reference to the flowchart illustrated in FIG. 12), if it is determined that the displayed moving image is not correct, other processing may be performed instead of the re-scanning. This can improve the efficiency of generation of data of a moving image regarding a fetus.

What is claimed is:

1. An ultrasonic diagnostic apparatus, comprising:
a display region setting unit configured to set a display region for displaying a 3D image;
a transmitting/receiving unit configured to transmit and receive ultrasound waves;
a first generating unit configured to control the transmitting/receiving unit to perform a 3D scanning on the display region, and generate volume data;
an analysis region setting unit configured to, on the basis of variance values of brightness information in the volume data, set a 3D analysis region to be used for calculation of a cycle of fluctuation over time, wherein the analysis region setting unit is configured to obtain a first region on a first single cross-sectional image included in the volume data out of a plurality of regions divided in a scanline direction on the first single cross-sectional image, where a temporal variance value of brightness information is higher than a first threshold, a second region on a second single cross-sectional image included in the volume data out of a plurality of regions divided in an orthogonal direction to the scanline direction on the second single cross-sectional image, where a temporal variance value of brightness information is higher than a second threshold, and a third region on a third single cross-sectional image included in the volume data out of a plurality of regions divided in an sweep direction on the third single cross-sectional image, where a temporal variance value of brightness information is higher than a third threshold, and set the 3D analysis region as a region formed by the first, second, and third regions;
an analyzing unit configured to, on the basis of the data on the 3D analysis region contained in the volume data, analyze fluctuations in signal intensity over time;
a calculating unit configured to, on the basis of the analysis result, detect a peak point of power, and calculate a cardiac cycle;
a second generating unit configured to, on the basis of the cardiac cycle and the volume data, generate a data set constructed by data with substantially equal cardiac cycles, and generate data sets corresponding to a plurality of cardiac cycles; and
a display configured to perform a rendering processing on each data set of the data sets into a 3D image set, and display the 3D images as a moving image.

2. The ultrasonic diagnostic apparatus according to claim 1, wherein the transmitting/receiving unit includes a mechanical 3D probe as an ultrasonic probe.

3. The ultrasonic diagnostic apparatus according to claim 1, further comprising a cross-sectional image generating unit configured to perform a 2D scanning with the ultrasound waves, and generate a cross-sectional image to set the display region, wherein the display displays the cross-sectional image.

4. The ultrasonic diagnostic apparatus according to claim 3, further comprising an input unit configured to be able to input a change operation about whether the moving image is to be changed or not, wherein the cross-sectional image generating unit performs the 2D scanning again if the moving image is changed by the input unit.

5. The ultrasonic diagnostic apparatus according to claim 1, wherein
the analysis region setting unit computes a variance value of brightness values at each vertically long area or horizontally long area on a scan cross-sectional image based on the volume data, and sets the 3D analysis region on the basis of an area having a variance value of the variance values beyond a threshold.

6. The ultrasonic diagnostic apparatus according to claim 1, wherein
the analysis region setting unit computes a variance value of brightness values at each vertically long area on a cross-sectional image orthogonal to a scan plane based on the volume data, and sets the 3D analysis region on the basis of an area having a variance value of the variance values beyond a threshold.

7. A controlling method of an ultrasonic diagnostic apparatus, comprising:
setting a display region for displaying a 3D image;
controlling transmission and reception of ultrasound waves to perform a 3D scanning on the display region, and generating volume data;
analysis region setting, on the basis of variance values of brightness information in the volume data, a 3D analysis region to be used for calculation of a cycle of fluctuation over time, wherein the step of analysis region setting includes obtaining a first region on a first single cross-sectional image included in the volume data out of a plurality of regions divided in a scanline direction on the first single cross-sectional image, where a temporal variance value of brightness information is higher than a first threshold, a second region on a second single cross-sectional image included in the volume data out of a plurality of regions divided in an orthogonal direction to the scanline direction on the second single cross-sectional image, where a temporal variance value of brightness information is higher than a second threshold, and a third region on a third single cross-sectional image included in the volume data out of a plurality of regions divided in an sweep direction on the third single cross-sectional image, where a temporal variance value of brightness information is higher than a third threshold, and setting the 3D analysis region as a region formed by the first, second, and third regions;
analyzing, on the basis of the data on the 3D analysis region contained in the volume data, a fluctuation in signal intensity over time;
detecting, on the basis of the analysis result, a peak point of power, and calculating a cardiac cycle;
generating, on the basis of the cardiac cycle and the volume data, a data set constructed by data with substantially equal cardiac cycles, and generating data sets corresponding to a plurality of cardiac cycles; and
performing a rendering processing on each data set of the data sets into a 3D image set, and displaying the 3D images as a moving image.

8. The controlling method of the ultrasonic diagnostic apparatus according to claim 7, wherein the controlling step includes transmitting and receiving the ultrasound waves by sweeping a mechanical 3D probe as an ultrasonic probe.

9. The controlling method of the ultrasonic diagnostic apparatus according to claim 7, further comprising performing a 2D scanning with the ultrasound waves, and generating a cross-sectional image to set the display region; and
displaying the cross-sectional image.

10. The controlling method of the ultrasonic diagnostic apparatus according to claim 9, further comprising inputting a change operation about whether the moving image is to be changed or not; and performing the 2D scanning again if the moving image is changed by the inputting step.

11. The controlling method of the ultrasonic diagnostic apparatus according to claim 7, wherein the step of analysis region setting includes computing a variance value of brightness values at each vertically long area or horizontally long area on a scan cross-sectional image based on the volume data, and setting the 3D analysis region on the basis of an area having a variance value of the variance values beyond a threshold.

12. The controlling method of the ultrasonic diagnostic apparatus according to claim 7, wherein the step of analysis region setting includes computing a variance value of brightness values at each vertically long area on a cross-sectional image orthogonal to a scan plane based on the volume data, and setting the 3D analysis region on the basis of an area having a variance value of the variance values beyond a threshold.

* * * * *